(12) United States Patent  
Neishaboori et al.

(10) Patent No.: US 9,418,421 B1  
(45) Date of Patent: Aug. 16, 2016

(54) AUTOMATION OF BIOPSY SPECIMEN HANDLING

(71) Applicants: Nastaran Neishaboori, Tehran (IR); Aria Pezeshk, Washington, DC (US); Azin Neishaboori, Fairfax, VA (US)

(72) Inventors: Nastaran Neishaboori, Tehran (IR); Aria Pezeshk, Washington, DC (US); Azin Neishaboori, Fairfax, VA (US)

( * ) Notice: Subject to any disclaimer, the term of this patent is extended or adjusted under 35 U.S.C. 154(b) by 0 days.

(21) Appl. No.: 14/866,848

(22) Filed: Sep. 26, 2015

(51) Int. Cl.  
*G06K 9/00* (2006.01)  
*G06T 7/00* (2006.01)  
*A61B 10/00* (2006.01)

(52) U.S. Cl.  
CPC .......... *G06T 7/0012* (2013.01); *A61B 10/0096* (2013.01); *G06T 7/0083* (2013.01); *G06T 2207/30024* (2013.01)

(58) Field of Classification Search  
None  
See application file for complete search history.

(56) References Cited

U.S. PATENT DOCUMENTS

| 4,528,187 | A | * | 7/1985 | Truglio | B01L 3/5082 356/246 |
| 4,568,424 | A | * | 2/1986 | Bauer | C10B 47/10 201/1 |
| 4,671,915 | A | * | 6/1987 | Fujimoto | B23P 15/001 137/246.21 |
| 5,383,472 | A | * | 1/1995 | Devlin | A61B 10/0096 378/164 |
| 5,609,827 | A | * | 3/1997 | Russell | A61B 10/0096 378/164 |
| 5,838,000 | A | * | 11/1998 | Mertesdorf | B82Y 20/00 250/216 |
| 7,177,459 | B1 | * | 2/2007 | Watanabe | B25J 9/1697 382/151 |
| 7,970,177 | B2 | * | 6/2011 | St. Hilaire | G01B 11/25 382/106 |
| 2002/0076355 | A1 | * | 6/2002 | Phifer | G01N 1/04 422/82.05 |
| 2004/0162639 | A1 | * | 8/2004 | Watanabe | B25J 9/1697 700/259 |
| 2011/0046455 | A1 | * | 2/2011 | Hengerer | A61B 5/055 600/309 |
| 2011/0208355 | A1 | * | 8/2011 | Tsusaka | B25J 9/1664 700/246 |
| 2014/0063241 | A1 | * | 3/2014 | Li | G06T 7/0008 348/143 |
| 2014/0371910 | A1 | * | 12/2014 | Hayashi | B25J 9/1697 700/259 |

FOREIGN PATENT DOCUMENTS

JP    2001027613 A  *  1/2001

OTHER PUBLICATIONS

Ground Robot Navigation using Uncalibrated Cameras, Koch et al, IEEE,978-1-4244-5040-4, 2010, pp. 2423-2430.*  
3D Time of Flight Sensors for Robot Navigation, Adil et al, Mobile Robot Design—Elec 6530 Fall 2011 Auburn University—Team No. 24, pp. 1-5.*

* cited by examiner

*Primary Examiner* — Jayesh A Patel

(57) ABSTRACT

The current disclosure is directed to the field of pathology, and the automated handling of biological specimens from containers containing clear solutions wherein the biological specimens reside. A computer-implemented method is disclosed for extracting specimens from such containers via an extraction device attached to a robotic arm. The robotic arm is controlled by a robotic system controller. The three-dimensional location of all specimens are estimated using image analysis techniques using images obtained from a plurality of imaging systems. Image analysis is used to simultaneously guide the extraction device and track the location of specimens inside the container.

20 Claims, 12 Drawing Sheets

AUTOMATION OF BIOPSY SPECIMEN HANDLING

BACKGROUND

1. Field

The present disclosure relates generally to automatic handling of biological specimens with the aid of signal processing.

2. Related Art

The application of automation techniques in handling pathology specimens that are collected in containers such as vials is expected to facilitate and expedite pathological practice, such as histologic examination, by reducing the turnaround time, and improving the consistency and efficiency of the operations, e.g. by reducing the frequency of operation errors, and even reducing contaminations. Additionally, automation is expected to free laboratory personnel from repetitive and monotonous tasks; decrease the costs associated with the training of bio-manipulation personnel; and decrease the dependency of bio-manipulation facilities on operational precision of tasks performed by different individual staff members. However, sample handling tasks are often complex, and require extensive care and precision. Accordingly, what is needed is to develop successful automated systems that overcome the inherent complexities involved.

Achieving a successful automated biopsy handing system requires developing accurate, efficient and robust techniques using image processing, automatic disposition of specimen extraction device (e.g. pipette), specimen extraction device pressure control to avoid causing damage to specimens (which may make subsequent diagnosis based on them less than fully reliable), a friendly user interfaces, and system calibration methods.

Replacing one container with a next container in a fixed position in the specimen handling system may be performed using standard mechanical operation automation mechanisms such as carousel or conveyor belt, as known by a person of relevant skill in the art.

Automated removal of container caps may also be performed using existing cap manipulating and removal methods as known to a person of relevant skill in the art.

Extracting specimens may be performed using extraction devices such as pipette or forceps or other devices, as known and appreciated by a person of relevant skill in the art. In an embodiment, extraction devices with different characteristics may be used to extract specimens of different type or size. For example, pipettes of different diameters may be used for specimens of different size.

The disclosure is not limited to the use of any specific cap removal mechanisms, specimen extraction methods and devices, and the method used for automatically transferring specimen containers in seriatim. Those skilled in the art would appreciate and recognize that any other method, currently known or developed in the future, may be used instead to perform the above functionalities.

Further embodiments, features, and advantages of the disclosure, as well as the structure and operation of the various embodiments, are described in detail below with reference to accompanying drawings.

1. BRIEF SUMMARY

In an embodiment, a computer-implemented method automatically "handles" pathology specimens residing in a container containing a clear liquid. Herein, we refer to extracting specimens from a container, and placing them inside a second container, as "handling specimens". By periodically obtaining image frames from the container containing the specimens in a clear liquid and applying image processing techniques, specimens are located inside the container, and an extraction device is guided to extract the specimens one by one from the container. The extraction device may be moved using an automated system, e.g. using a robotic arm attached thereto. Since the location of the specimen to be extracted may change due to the movement of the extraction device inside the container, the location of specimens is tracked using a tracking algorithm.

In an example embodiment, specimens are initially residing inside a container, e.g. a vial, filled with a clear liquid such as diluted formalin, wherein the container is labeled with a patient's information and also specimen specific information, such as the location of the body the specimen was extracted from, and the time of extraction. In this example, the label on the container is scanned to retrieve recorded information, and based on the information retrieved from the container's label, information is printed on a second container such as a cassette. Subsequently, the cap covering the container is removed and specimens are individually extracted from the container. Each extracted specimen is subsequently placed in a separate cassette, wherein each cassette has information corresponding to the enclosed specimen printed directly on it, such that it is readable by a scanning device.

Each such label may comprise a computer readable code, such as a bar code, and may be used to access or update patient and specimen specific information on a computer database. Typically, all the specimens in one container belong to one patient. For example, all the specimens in a container may be surgically extracted from a small area of one patient's body. One patient may have more than one assigned container, for example when there are multiple general locations in a patient's body from which biopsy specimens are extracted. In an example, there may be up to 20 samples in one container. However, the instant disclosure works for any number of specimens in a container. The dimensions of each specimen are typically in the range of 1 millimeter cubed ($mm^3$) to 10 $mm^3$, although this may not always be the case. For example, endoscopic biopsy samples are typically cuboids and have a volume in the range of about 2-7 $mm^3$, whereas shave biopsies (skin biopsies) typically have elliptical or circular cross sections of up to 10 mm in diameter, and 1 millimeter (mm) thickness, and needle core biopsies are typically of long cylindrical shapes and about 1 mm in diameter and 10-20 mm in length.

The specimens collected from a biopsy process are typically semi-solid. As such, it is important to handle them with care, in order to avoid crushing or damaging them.

The clear liquid inside the container may be selected based on the type of processing that is to be performed on the specimens. For example, for histology processes, a diluted formalin solution may be used. In another example, glycerol may be added to distilled water, or to a diluted formalin solution. In one example, the clear liquid inside the container may be of a specific color in order to improve the visibility of specimens residing in the container, and to facilitate image processing.

It is sometimes preferred that the container is shaken before cap removal in order to ensure that no specimen that may be incidentally attached to the cap is missed.

The systems and methods disclosed herein do not depend on any specific specimen size, a specific number of specimens in one container, the type of clear liquid used in a container, or the size or shape of the container.

The disclosure requires that the container being processed becomes fixed in one location during the specimen extraction process. This helps maintaining the accuracy of the estimations obtained on the location of the specimens inside the container. After extraction of all specimens, the container with no other specimens is removed from the fixed position, and replaced by a new container which also contains one or more specimens in a clear liquid. It is also important that the extraction device is cleaned properly, or replaced after extracting specimens from one container, in order to ensure that no cells pertaining to specimens in one container are carried over to other containers. For example, in case of using pipettes to extract specimens, disposable pipette tips may be used. In this example, a pipette tip may be discarded after being used to extract specimens within one container, and replaced with a new one for extracting specimens from another container.

2. BRIEF DESCRIPTION OF THE DRAWINGS

The accompanying drawings, which are incorporated herein and form part of the specification, illustrate the present disclosure and, together with the description, further serve to explain the principles of the disclosure and to enable a person skilled in the relevant art to make and use the disclosure.

Figure 2:
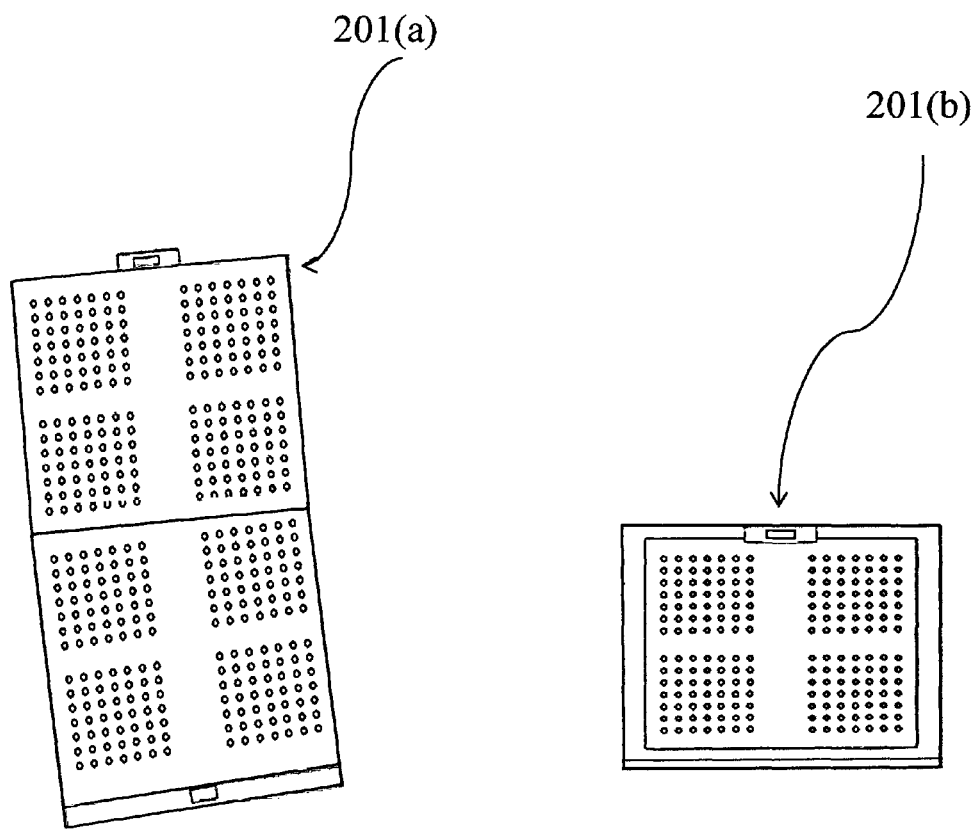

FIG. 2 displays a typical cassette, frequently used to house individual extracted specimens after removal from an initial container containing clear liquid.

Figure 3A:
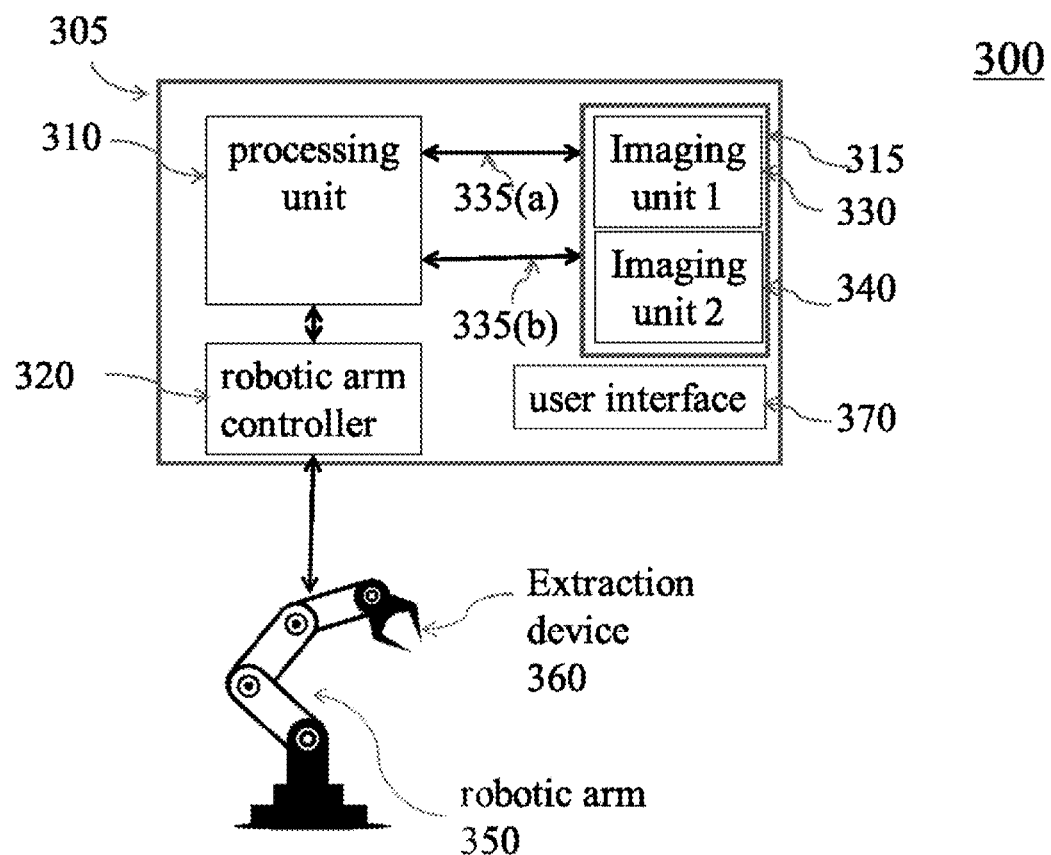

FIG. 3A is a diagram that illustrates the different modules of the automatic specimen extraction system according to an embodiment of the disclosure.

Figure 3B:
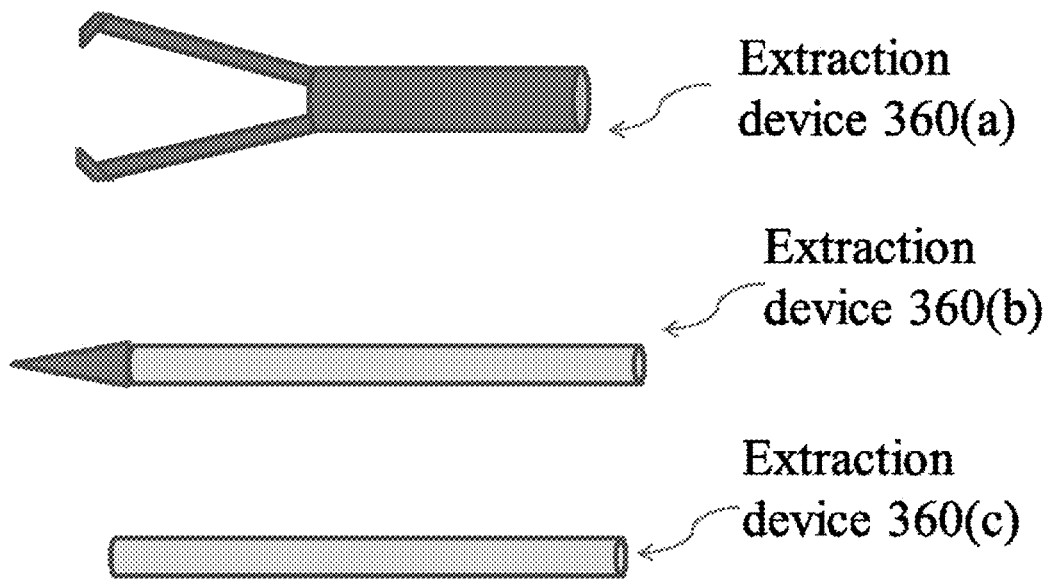

FIG. 3B displays example extraction devices that may be used for specimen extraction according to an embodiment of the disclosure.

Figure 4:
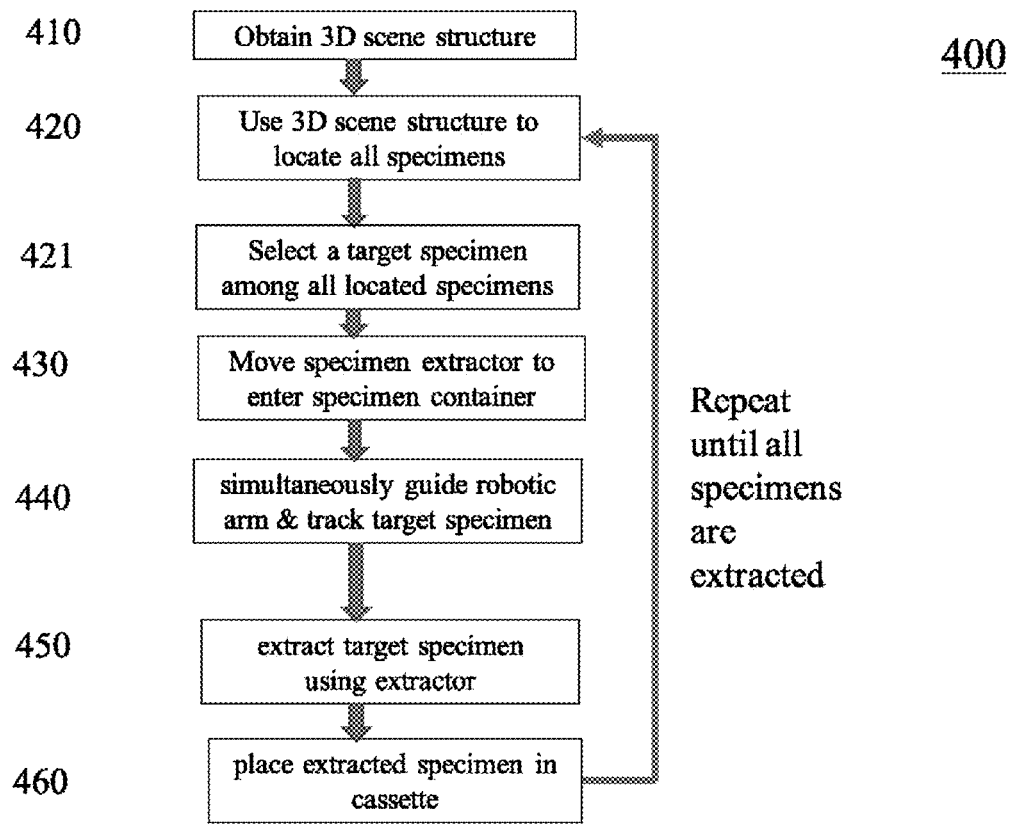

FIG. 4 is a flowchart that illustrates the operation of the disclosed automated specimen handling, according to an embodiment of the disclosure.

Figure 5:
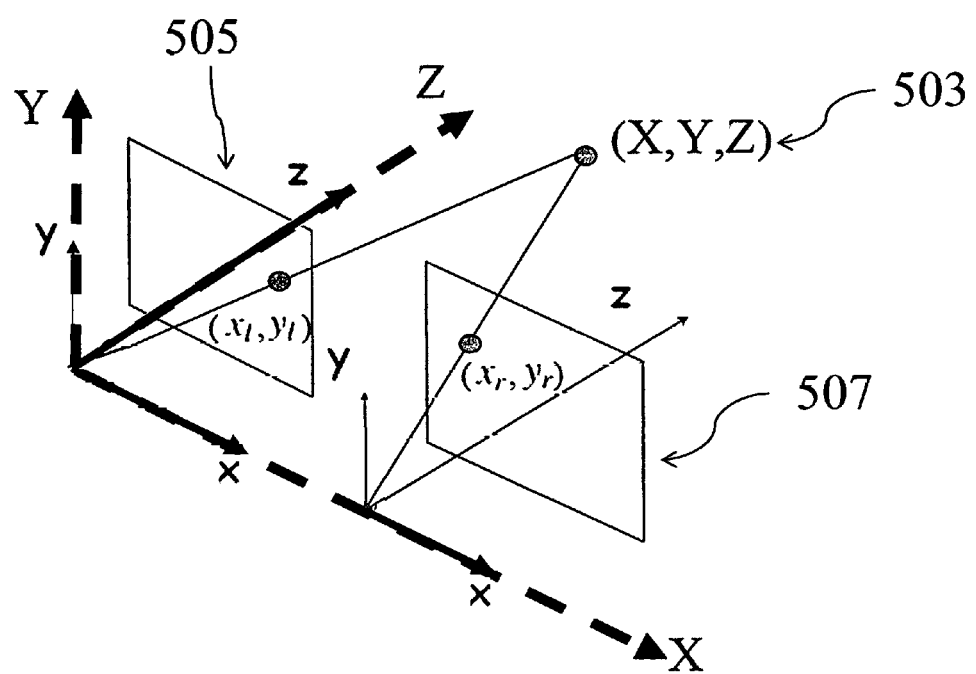

FIG. 5 is a diagram that illustrates an example of the projection of a 3D point onto 2D image planes of a stereo system, which may be used according to an embodiment of the disclosure.

Figure 6:
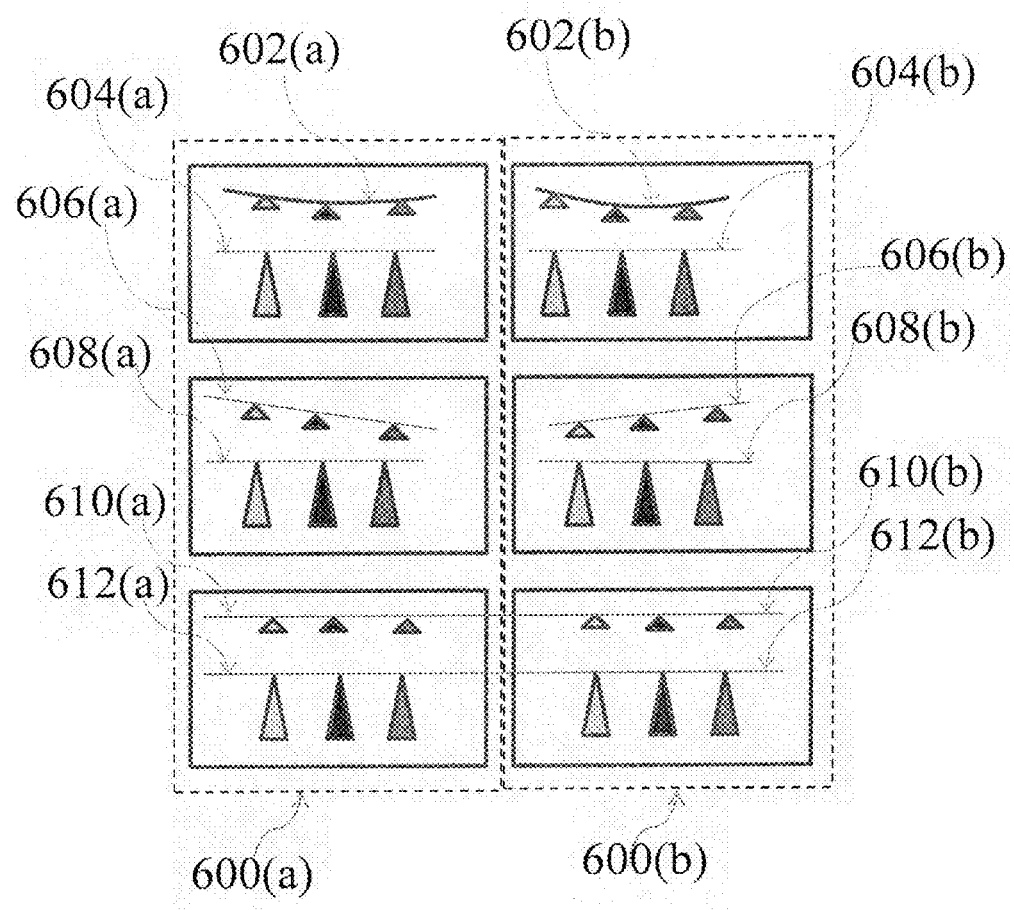

FIG. 6 is a diagram that illustrates an example of an image rectification process, which may be used according to an embodiment of the disclosure.

Figure 7A:
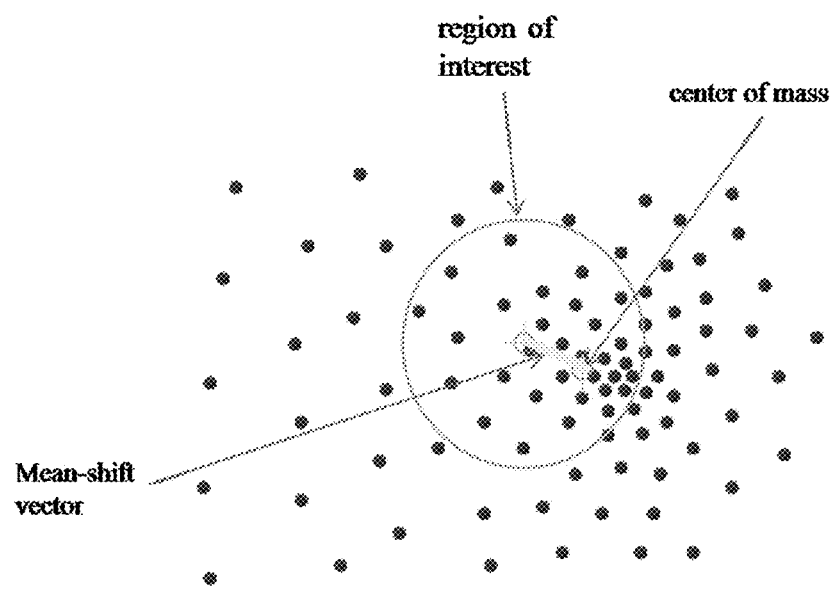

FIG. 7A is a diagram that illustrates an example progression of mode seeking using mean-shifting algorithm which may be used according to an embodiment of the disclosure.

Figure 7B:
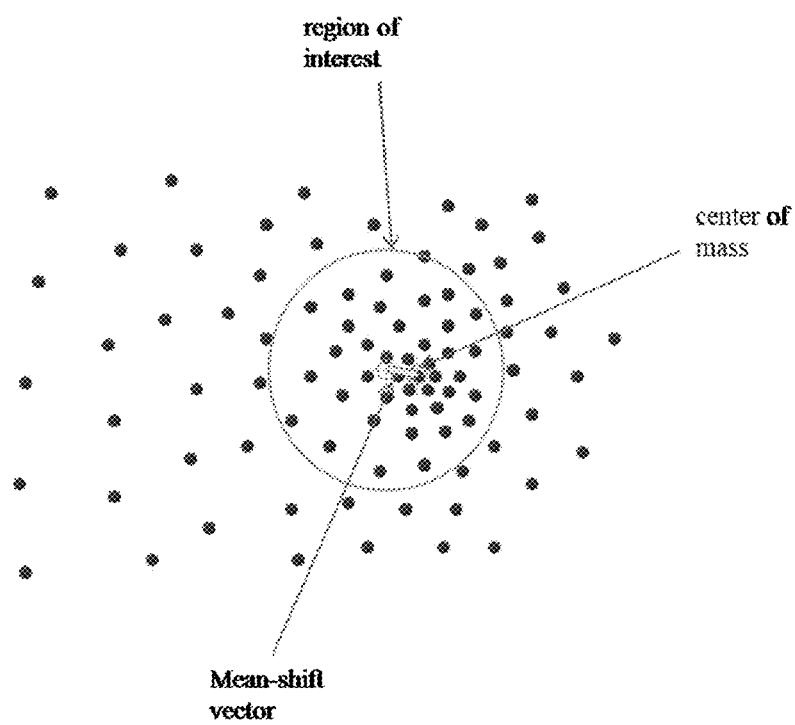

FIG. 7B is a diagram that illustrates another view of the example progression of mode seeking using mean-shifting algorithm, which may be used according to an embodiment of the disclosure.

Figure 7C:
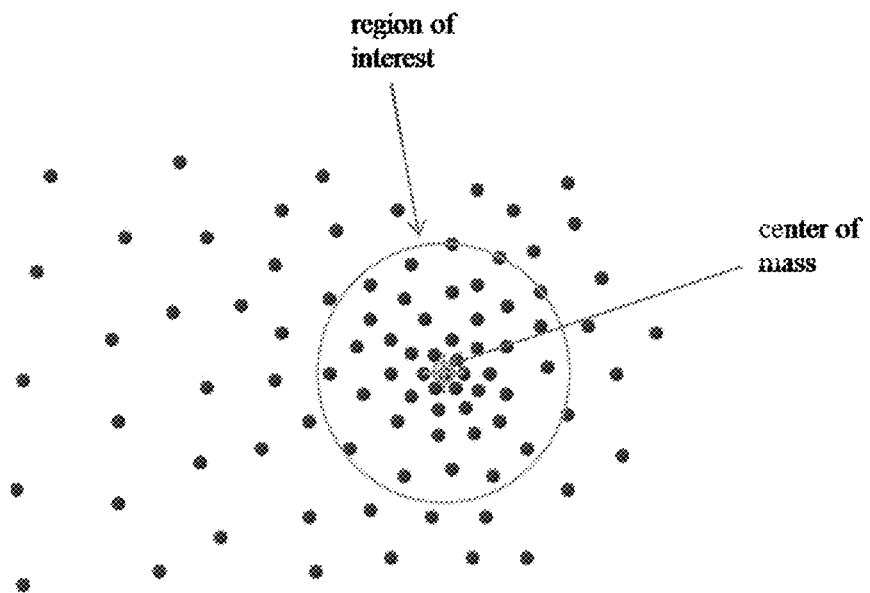

FIG. 7C is a diagram that illustrates yet another view of the example progression of mode seeking using mean-shifting algorithm, which may be used according to an embodiment of the disclosure.

Figure 8:
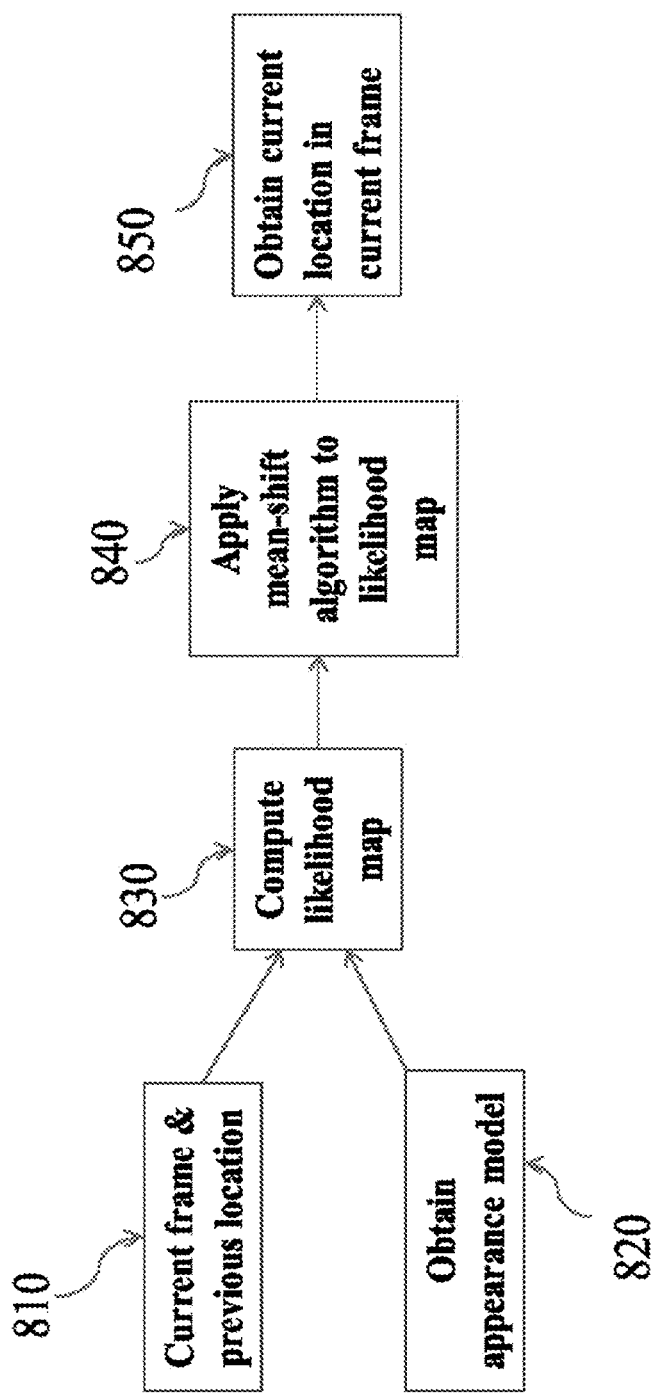

FIG. 8 is a diagram that illustrates the overview of tracking an object in a video using mean-shift algorithm which may be used according to an embodiment of the disclosure.

3. DETAILED DESCRIPTION

An embodiment of the current disclosure aims to facilitate automating the following procedure for the physicians and technicians handling biopsy or other semi-solid biological specimens: (i) provide a tray of labeled and capped containers containing biological specimens (in a clear liquid), (ii) have containers automatically removed one by one from the tray, (iii) have each container processed, (where the container has specimens belonging to one person/body location) by extracting from the container all specimens floating or otherwise residing therein, (iv) place an specimen extracted from the labeled container containing clear liquid into another labeled container such as a labeled cassette, where the label comprises name and identification of a patient, and optionally a computer readable code such as bar code.

Figure 1A:
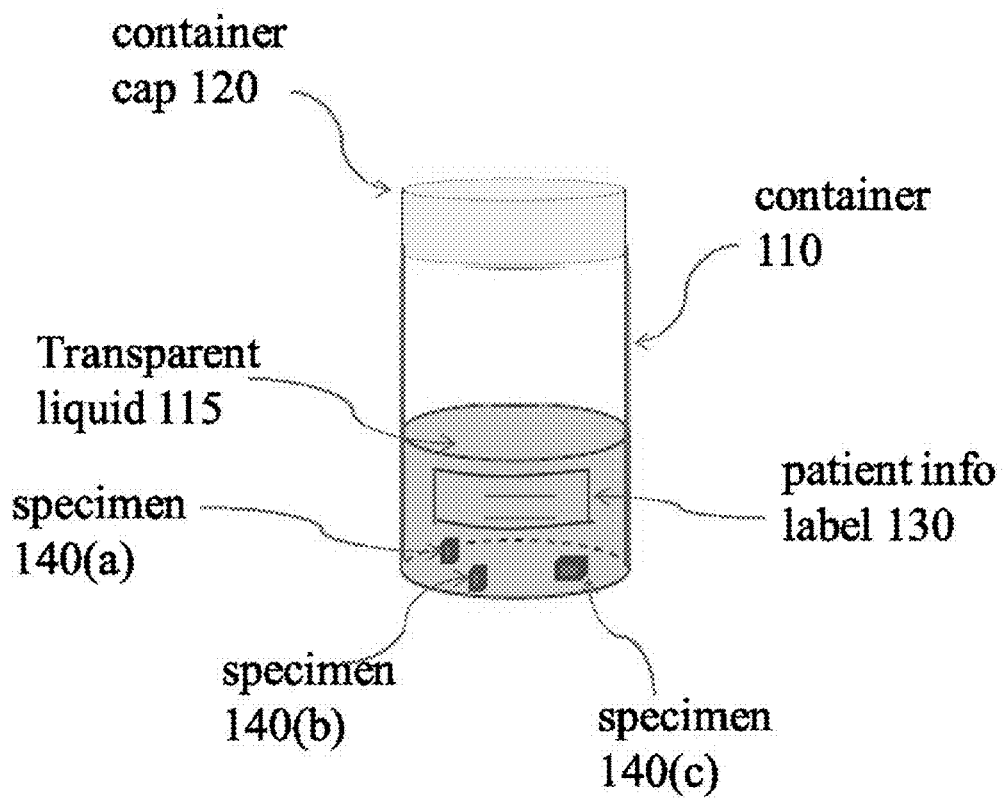
FIG. 1A is a diagram illustrating a typical container that contains biological specimens to be extracted.
Figure 1B:
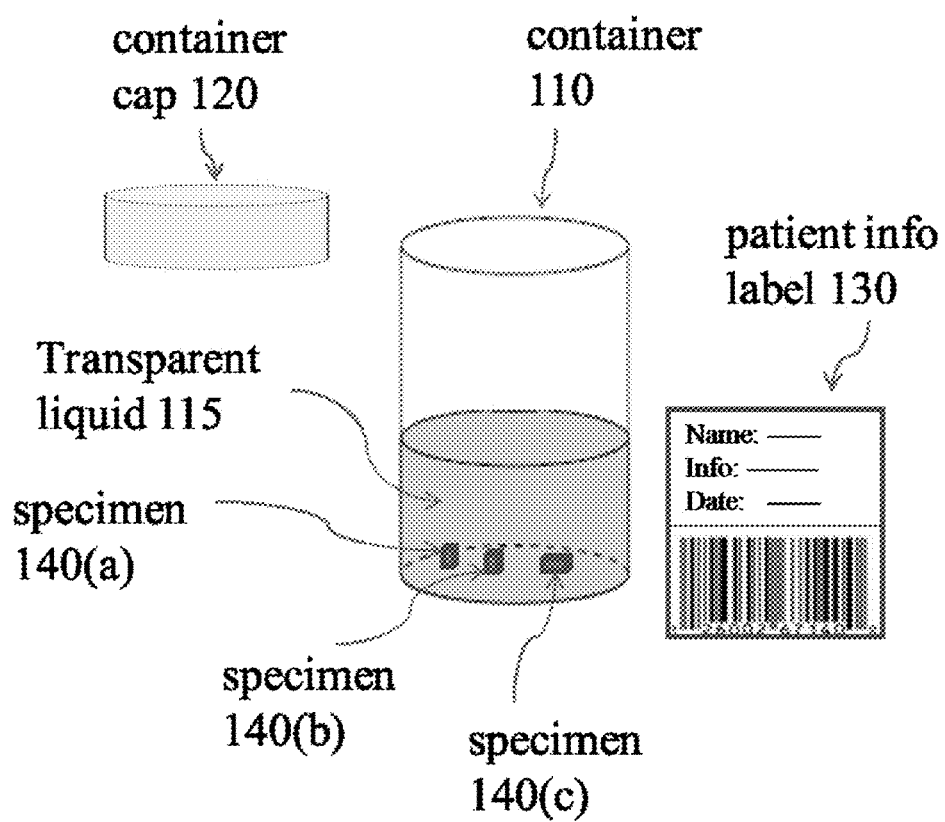
FIG. 1B is a diagram illustrating the components of a typical container that contains biological specimens to be extracted.

FIGS. 1A and 1B displays a typical container 110, used to contain one or more specimens 140 in a transparent liquid 115, with a label 130 attached thereto, wherein the label comprises a computer readable code, e.g. a bar code, which may be associated with a patient, and a specific area of the patient's body from where the specimens were surgically removed, and the time of the surgical removal, as can be seen in detail in FIGS. 1A-1B. FIG. 1A illustrates the container 110 closed with cap 120 and the label 130 attached. FIG. 1B illustrates the components shown in FIG. 1A separately. In an example, container 110 may have a diameter of 22 millimeter to 30 millimeter, and a height of 20 millimeter to 50 millimeter.

A skilled artisan would appreciate that whether a specimen (e.g. specimen $140(a)$ or $140(b)$ or $140(c)$) floats or sinks in the liquid 115 inside the container 110 is determined by the density of the specimen relative to the density of the liquid 115. For example, the density of 10% buffered formalin liquid is close to that of water (1 g/mL) at room temperature (around 25° C.). However, the density of glycerol is greater than that of water (about 1.26 g/mL at room temperature). The density of biological specimens may vary depending on the part of body they are removed from, e.g. bone (about 1.75 g/cm$^3$), soft tissue (about 1.06 g/mL), fat (0.9 g/mL), etc. The instant disclosure is not limited to the cases that the specimens float in the liquid filling the container or settle at the bottom of the container, and may be used in either condition.

FIG. 2 displays two different views of a typical cassette indicated as $201(a)$ and $201(b)$. Such a cassette is frequently used to house individual extracted specimens after removal from the initial container (e.g. container 110). As mentioned above, it is typical to have a code pertaining to patient information and the specimens collected from the patient printed directly on a cassette that is to enclose each such specimen.

FIG. 3A illustrates the different modules of the automatic specimen extraction system according to an embodiment of the disclosure. Extraction processing system 305 comprises a plurality of imaging units, e.g. two imaging units 330 and 340, that are used to acquire images from an open container e.g. container 110, as will be further described shortly. Extraction processing system 305 further comprises a processing unit 310 that is communicatively coupled with imaging units 330 and 340 using communication paths $335(a)$ and $335(b)$ respectively. In an example, the communication paths $335(a)$ and $335(b)$ may be realized via a communication bus. Processing unit 310 receives the acquired images from imaging units 330 and 340. In an example, imaging units 330 and 340 may be Charged-Couple Device (CCD) cameras. In another example, imaging units 330 and 340 may be infrared cameras, or other imaging systems as recognized and appreciated by a skilled artisan. Herein we use the terms camera, imaging system and imaging unit interchangeably.

In an embodiment, imaging units 330 and 340 are capable of obtaining images periodically at a high frame rate, e.g. 10-20 frames per second. Imaging units 330 and 340 are synchronized and obtain image frames from the container simultaneously. Processing unit 310 computes different information based on these images, as will be described in detail shortly with respect to FIG. 4, and sends commands to robotic arm controller 320, to which it is communicatively coupled. In an example, the communication between processing unit 310 and robotic arm controller 320 may be via a communication bus. In an example, the communication between processing unit 310 and controller 320 may be via a wired cable or wireless communication. Robotic arm controller 320 may in itself comprise a processing unit. Robotic arm controller 320 is communicatively coupled to robotic arm 350, which can receive motion commands from robotic arm controller 320, and move according to those commands. A variety of techniques on controlling and stably moving a robotic arm to a prescribed location or in a prescribed direction and/or for a prescribed distance using a robotic arm controller are known and understood by a skilled artisan. Accordingly, robotic arm controller 320 and robotic arm 350 may be implemented using methods known to a person of relevant skill in the art. In an embodiment, robotic arm controller 320 is integrated with the robotic arm 350 in one unit. In another embodiment, robotic arm controller 320 is integrated with processing system 305.

Still considering FIG. 3A, robotic arm 350 has an extraction device 360 attached thereto, which is used to extract specimens from a container such as container 110, and place them in a cassette, e.g. the cassette displayed in FIG. 2. Extraction device 360 may be a pipette, a forceps, or any other extraction device, as known to a person of ordinary skill in the art. The extraction device 360 is selected to have a small enough volume such that its entrance into the container, e.g. container 110, does not result in the overflow of the liquid within the container (i.e. to spill out).

Still considering FIG. 3A, in an embodiment, a user interface 370 may be used to receive input from an operator. For example, the user interface may be a touch screen displaying the image obtained by one or more imaging units, e.g. imaging unit 315 and/or imaging unit 340. This screen may be used by the operator to locate and select the specimens of interest that are to be extracted. In another example, the operator may identify one or more specimens within the container as garbage, due to various factors such as being too small or atypical. The inputs from the operator may be used to accurately locate the specimens in the image frames obtained from one or more imaging units. In an example, the location of the specimens are first obtained from processing the image frames obtained from one or more imaging units according to the methods described in FIG. 4, and the inputs from the operator may be subsequently used to confirm or verify those locations.

FIG. 3B shows examples of extraction device 360. In an example embodiment, extraction device may apply an adjustable level of grasp according to the type of specimen(s) that are to be extracted. For example, different levels of pressure may be applied by the forceps device 360(*a*) in order to extract specimens of different texture or sensitivity to pressure. In another example, extraction device 360 may be a pipette, such as pipette 360(*b*) with a tip diameter smaller than the size of the specimen being extracted. In this example, the specimen is extracted by applying suction to the specimen being extracted by positioning the tip of the pipette on the specimen. Techniques for automatic control of pipettes are known to a person of relevant skill in the art. In another example, extraction device 360, e.g. pipette 360(*c*) may be a pipette with a tip diameter larger than the size of the specimen being extracted. In this example, the pipette will swallow the extracted specimen and contain it within. In yet another example, extraction device 360 may be a suction device. In this example, to be able to successfully grasp the target specimen inside the container, the Euclidean distance between the tip of the suction device and the target specimen is required to be smaller than a pre-determined value, e.g. 1 millimeter.

Directing to FIG. 4, a method and process according to an embodiment of the disclosure at a high level is illustrated comprising the steps involved in detection and tracking of pathology specimens for automatic extraction. These steps are further described with respect to FIGS. 5, 6, 7A-7C, and 8.

In step 410, 3-dimesional ("3D") scene structure of specimens in the container (e.g. container 110) is computed. In an embodiment, stereo imaging systems are used to compute the 3D scene structure. For example, imaging unit 330 and imaging unit 340 may be used in step 410. Computations performed to obtain the 3D scene structure of specimens within the container containing clear liquid and the specimens (e.g. container 110) are performed in a processing unit, such as processing unit 310.

Still considering FIG. 4, in step 420, target segmentation is applied on image frames, e.g. image frames obtained from imaging unit 330 and imaging unit 340, to locate all specimens within the container, e.g. container 110.

In step 421, a target specimen is selected from within the container, e.g. container 110. In an example, the target specimen is selected from a plurality of specimens within the container, e.g. container 110. In an embodiment, the specimens have a density smaller than that of the density of the fluid within the container (such as container 110) and thus float in the liquid in the container. In an example according to this embodiment, specimens within the container are extracted based on their z-coordinate. That is, the top-most specimen is to be extracted first, and the second top-most specimen is to be extracted second, and so on.

In an embodiment, the specimens have a density greater than that of the fluid within the container (e.g. container 110), and thus settle at the bottom of the container. In an example according to this embodiment, selecting a target specimen from a plurality of specimens may be based on a random sequence of located specimens. In another example, an exact or heuristic solution to a traveling salesman problem may be found to obtain a sequence of specimens from which target specimens are selected sequentially. Notably, the procedure for locating and selecting specimens that settle at the bottom of a container also requires 3D information, as specimens are themselves three-dimensional, and their height from the bottom of the container is required to be obtained for an extraction device to be accurately to guided to the location of the specimens.

The actions carried in steps 420 and 421 may be performed using one or more processing units (such as processing unit 310).

Still considering FIG. 4, in step 430, an extraction device, such as extraction device 360(*a*) or 360(*b*) or 360(*c*), is entered in the first container to extract the target specimen. In an embodiment, the extraction device is attached to a robotic arm, such as robotic arm 350.

Still considering FIG. 4, in step 440, image frames are periodically obtained by imaging units, e.g. imaging units 330 and 340. In an embodiment, stereo vision is used to simultaneously guide the robotic arm inside the container containing the specimens, e.g. container 110, and to track the selected target specimen which may move due to the motions of the extraction device within the container.

In an embodiment, the specimens float in the container (due to the density of the specimens being smaller than the density of the liquid 115 within the container 110). In a laminar (non-turbulent) liquid, the displacement of the target specimen occurs mostly at the direction of the motion of the extraction device, as would be recognized by a skilled artisan. For example, when a pipette approaches a floating target specimen from above in the z-direction, the floating target specimen may move further down in the z-direction. The conditions required to maintain the liquid in a laminar state are further described shortly with respect to FIG. 8. Again, one or more processing units (such as processing unit 310) may be used to perform the operations in step 440.

There may also be cases wherein some specimens float in the liquid 115 within the container 110, while some other specimens settle in the bottom. In these cases, a hybrid of the two target selection method described above may be used. For example, first the floating specimens are extracted, starting from the top-most specimen. Afterwards, the settling specimens may be removed based on a random selection scheme or traveling salesman.

In step 450, the target specimen is extracted using an extraction device (e.g. extraction device 360(*a*), 360(*b*) or 360(*c*)), which may be attached to a robotic arm, e.g. robotic arm 350. If there are more specimens left in the first container, the process then jumps back to step 420 and repeats the subsequent steps, until all specimens are removed from the first container. Details of steps 410, 420, 430 and 440 are further described shortly.

The specimen extraction of step 450 may be done using any specimen extraction method known to a person of ordinary skill in the art, such as via forceps, pipette, etc. that may be attached to the robotic arm and be controlled and operated by the robotic arm.

In step 460, the extracted specimen is placed in a second container, e.g. a cassette (such as the cassette shown in FIG. 2), located in a position different than the first container and labeled with information corresponding to the information located on the label attached to the first container. The movement of robotic arm from the first container to the second container, and the disposal of the extracted specimen to the second container are realized using processing unit 310 and robotic arm controller 320, using automation techniques known to a person of ordinary skill in the art.

In the following, steps 410-450 are described in further detail.

A. Computing the 3D Scene Structure (Step 410)

Depth information in a scene is lost when the three-dimensional ("3D") scene is projected onto a 2D plane during image capture by an imaging system, such as camera or an ultrasonic imaging device. Therefore, while the two-dimensional ("2D") location of a point in an image can be obtained using a single camera, if the absolute location and direction of the single camera can be easily obtained, in order to extract the 3D scene structure, at least two cameras are required. Prior knowledge about the position of cameras relative to each other and relative to the scene can subsequently be used to obtain a depth map.

In an embodiment, it is possible to use structured light, which involves projecting a pre-designed pattern of light (e.g. parallel grids or speckled patterns) with visible or invisible wavelengths onto the scene. This may be helpful particularly when the objects in the scene consist mostly of smooth surfaces that might pose difficulty in finding the correspondence between same points pictured by different cameras. The importance of the correspondence problem will be discussed below.

In an embodiment, stereo vision is used to infer depth of objects in the scene. In stereo vision, images taken from the same scene using the two cameras are compared using multi-view geometry (also known as epipolar geometry). In the design disclosed herein, camera positions, types, distances and angles relative to each other and to the scene are known. A calibration process may be used to obtain the cameras' intrinsic and extrinsic properties. This knowledge may be used as discussed below to obtain the correspondence between same points as captured by the two cameras, and thereby the depth of each point in the scene.

The general steps involved in finding depth from stereo vision are as follows:

a) A pair of images captured simultaneously from the same scene are obtained. Frames of video obtained at the same time by two cameras are matched against each other to obtain depth information from the scene in real time. The area where an object is only visible in one of the cameras and not the other one is commonly referred to as a dead zone. The cameras are therefore placed at a distance such that the specimen cup is outside of the dead zone of the two cameras so that depth information can be calculated. FIG. 5 illustrates an example of the projection of a 3D point onto 2D image planes of a stereo system. Specifically, FIG. 5 shows a 3D point (X, Y, Z) indicated by 503 that is projected onto two different planes, a left-hand side plane 505 and a right-hand side plane 507. The projection of 3D point (X, Y, Z) (indicated by 503) on the left-hand side plane 505 is indicated by $(x_l, y_l)$. The projection of 3D point (X, Y, Z) (indicated by 503) on the right-hand-side plane 507 is indicated by $(x_r, y_r)$.

b) Due to various distortions such as the optics of the cameras, epipolar lines could reside along curves. The frames from the cameras are therefore rectified so that the epipolar lines in the resulting images become linear and aligned with one another. An example image rectification process is illustrated in FIG. 6. In this figure, in the first row of 600(*a*) and 600(*b*) (corresponding to the left and right images respectively), it can be seen that the left and right images, and sample epipolar lines 602(*a*) and 602(*b*) are curved due to image distortions and not parallel to sample epipolar lines 604(*a*) and 604(*b*) respectively. In the second row of 600(*a*) and 600(*b*), the left and right images are again displayed after removal of image distortions. Sample straightened epipolar lines 606(*a*) and 606(*b*) are also displayed in the second row of 600(*a*) and 600(*b*) respectively. As can be seen, sample epipolar lines 606(*a*) and 606(*b*) are straight, but are not parallel to sample epipolar lines 608(*a*) and 608(*b*) respectively. In the third row of 600(*a*) and 600(*b*), the left and right images are displayed after rectification. Also, sample aligned epipolar lines 610(*a*) and 610(*b*) are also displayed in the third row. As can be seen, sample epipolar lines 610(*a*) and 610(*b*) are aligned and in parallel with sample epipolar lines 612(*a*) and 612(*b*).

c) For each point $P_{\{i,j\}}^1$ in image from first camera, the point $P_{\{u,v\}}^2$ in the image captured by the second camera is found that corresponds to this point. In one embodiment, a block of pixels around $P_{\{i,j\}}^1$ are extracted (e.g. a 7×7 block of pixels around each pixel of interest). The 2D cross correlation with blocks of pixels along a line in the second image is used to find the counterpart of $P_{\{i,j\}}^1$ in the image from the second camera.

d) A disparity map is computed based on the correspondence of points between rectified images from the two cameras, and the relative displacement of points observed by the two cameras. For example, a disparity map may be obtained based on the point correspondence between pixels in two images captured simultaneously from the same scene. The depth of points in the 3D scene structure can then be computed based on this disparity map, and the a priori information about the cameras and their relative positions. This process is commonly referred to as re-projection, and in short, is based on the principle that the depth of a point in a scene is inversely proportional to the difference in distance of corresponding image points.

In an example embodiment, in order to speed up the search process and increase robustness of the stereo system in obtaining more accurate disparity maps over smooth surfaces, additional steps may be taken in resolving the point correspondence problem. For example, these steps may include an algorithm that uses local plane sweeps based on initial sparse feature correspondences, or multi-scale point correspondence along more physically relevant image features such as edges, as known and appreciated by a person of relevant skills in the art.

B. Target Segmentation and Target Selection (Steps 420-421)

Once the 3D scene structure has been obtained, this information is used to select the target specimen. In an embodiment, wherein the density of specimens (e.g. specimens 140 (*a*)-140(*c*)) is smaller than the density of the liquid within the container, e.g. container 110, and the samples float in the liquid 115 inside the container 110, the topmost specimen in the specimen container may be selected for extraction.

In an embodiment, wherein the density of specimens is greater than the density of the liquid within the container, and the samples settle in the bottom of the container, extraction may start from any of the specimen in the container. For example, the leftmost specimen in the container 110 may be first selected for extraction. After extracting the first specimen, a sequence of targets to be extracted may be generated using a variety of schemes. For example, a sequence of targets may be generated randomly. Alternatively, in an example embodiment, a sequence may be generated by finding an exact or approximate solution to a traveling salesman problem.

Traveling salesman problem finds the shortest path than can be taken from an initial vertex such that all vertices are visited at least once before reaching the initial vertex again. Traveling salesman problem may be modelled as an undirected weighted graph, wherein cities are the graph's vertices, and paths are the graph's edges, and wherein a path's distance is the edge's length. It is a minimization problem starting and finishing at a specified vertex after having visited each other vertex exactly once. Often, the model is a complete graph (i.e. each pair of vertices is connected by an edge). Traveling salesman problem may be formulated as an integer linear program. As it would be recognized by a skilled artisan, while finding the exact solution to traveling salesman problem is NP-complete, if the number of samples in the container are reasonably small (3-4), an exact solution may be attainable in a short amount of time. Sub-optimal solutions may alternatively be found using heuristic algorithms, e.g. Christofides's algorithm, as is known to a person of relevant skill in the art. In the example embodiment wherein a sequence of target specimens is generated based on an exact or approximate solution to a traveling salesman problem, the center of mass of the horizontal cross-section of each specimen (or an approximation of it) may be used to represent a vertex to be traversed. For example, if the cross-section of a specimen is approximately a rectangle, the cross-section of the specimen is approximated by the rectangle, and the center of mass of the rectangle may be used to represent a vertex to be traversed in a traveling salesman problem. In another example, if the cross-section of a specimen is close to an ellipse, the cross-section of the specimen is approximated by the ellipse, and the center of mass of the ellipse may be used to represent a vertex to be traversed in a traveling salesman problem. Approximating the cross-section of a specimen with one of the known two-dimensional basic geometrical shapes e.g. a circle, square, rectangle, ellipse, parallelogram, or diamond is known to a person of relevant skill in the art.

To identify and locate specimens, a combination of the 3D scene structure and edge detection may be used. In an embodiment, edge detection is used in the image obtained from one of the cameras. Short and erroneous edges are then pruned, and discontinuities along the edges are filled using anisotropic contour completion, as is known to a person of relevant skill in the art. In an example, the number of detected specimens may be of interest, and may be recorded.

In an example embodiment wherein the specimens float in the liquid within the container (e.g. container 110), the topmost closed-loop set of edges may be subsequently identified as belonging to the top specimen in the container. Prior knowledge about the general size of the specimens may be used to merge or split the detected surfaces as needed to obtain more accurate results.

In an example embodiment wherein specimens settle in the bottom of the container, the target specimen is selected from among the set of all closed-loop set of edges according to a scheme such as random or based on the solution to a traveling salesman problem.

In an embodiment, the size of the specimens may be computed by measuring the size of the above described identified closed-loop set of edges in the image. It is recognized by a person of relevant skill in the art that the actual specimen size may be found using the following:

specimen size in the image=actual specimen size*focal length of imaging system/specimen distance from imaging system Since the specimen size in image may be easily identified in number of pixels, and that the real size of one pixel and the focal length in a particular imaging system (e.g. imaging unit 330 or 340) are available, the actual size of a specimen may be obtained. Optionally, if the size of a specimen is determined to be smaller than a pre-determined value, it may be considered garbage, and eliminated from the extraction process. If the specimen selected as target specimen is garbage, a second target specimen may be selected. As each specimen gets extracted this process is repeated by extracting the next selected specimen until all samples have been successfully extracted.

C. Extraction Device Entry and Object Tracking (Steps 430 and 440)

Once a target specimen has been selected using information from the 3D scene structure, the extraction device enters the specimen container and moves towards the target. The 2D locations of the robotic arm and the target specimen are tracked throughout the extraction process based on frames of video from one of the cameras. The movement of the extraction device in x and y coordinates is therefore controlled based on coordinates provided from a single camera, but the extraction device is guided in the z direction according to the depth information as calculated throughout the procedure using frames from both cameras as described earlier. In one embodiment of the tracking algorithm, mean shift algorithm is used to track the motion of the specimen during extraction, as would be known and understood by a skilled artisan.

Mean shift is a robust mode-seeking algorithm that is also used commonly for tracking of non-rigid objects (i.e. those whose shapes might change over time). Consider a set S of d dimensional data points $x_i$=1, 2, ..., n, and let K(x) be a kernel function that determines the contribution of point $x_i$ to the estimation of the sample mean defined as below:

$$m(x) = \frac{\sum_{i=1}^{n} K(x - x_i) x_i}{\sum_{i=1}^{n} K(x - x_i)}$$

The difference m(x)−x is called the mean shift. At each iteration of mean shift, a data point is moved to the location of its mean, and the algorithm stops when the mean shift computed in that iteration equals 0, or falls below a certain threshold. Several types of kernels are often used to properly weight the contributions of points based on their distance relative to the current point, including the flat kernel:

$$K(x) = \begin{cases} 1, & \text{if} \|x\| \leq \alpha \\ 0, & \text{if} \|x\| > \alpha \end{cases}$$

And the Gaussian kernel:

$$K(x) = \frac{1}{\sqrt{2\pi}\,\sigma^d} e^{-0.5 \frac{\|x\|^2}{\sigma^2}}$$

FIGS. 7A-7C show the progression of mean shift using a graphical example, starting in FIG. 7A, proceeding as illustrated in FIG. 7B, and terminating as illustrated in FIG. 7C. When using mean shift for tracking, the object of interest may be described by its template, or histograms of color, intensity, or edge histograms.

In an embodiment intensity histograms are used to obtain an object model. In this embodiment, the object model is defined similar to a probability density function (PDF) by dividing the counts of pixels in each intensity bin by the total number of pixels contained within its window. In subsequent frames of video where the location of the object needs to be tracked, intensity histograms are computed for windows of pixels in the vicinity of the location of the object in the previous frame. Each histogram is then normalized as described above to obtain a PDF. The similarity between each of these normalized histograms and the normalized histogram of the object of interest is then computed using the Bhattacharyya coefficient as follows:

$$\rho = \Sigma_{u=1}^{m} \sqrt{p_u q_u}$$

Where p and q are the vectors of normalized histograms of a window in the current frame and the object model, respectively. This distance is equivalent to the cosine of unit vectors $(\sqrt{p_1}, \sqrt{p_2}, \ldots, \sqrt{p_m})$ and $(\sqrt{q_1}, \sqrt{q_2}, \ldots, \sqrt{q_m})$, and a higher value means a better match between the PDFs of a window and the object model.

FIG. 8 shows an overview of object tracking in consecutive video frames using mean shift algorithm. Using the object model (appearance model) obtained and the distances computed above in 820, the current frame of video in 810 is converted into a likelihood map in 830. Mean shift is applied to this likelihood map (sometimes referred to as histogram back-projected image) in 840 to find the location of the object in current frame. The location of the object is then moved to its new location found in the current frame, and the process is repeated for all subsequent frames of video to track the object.

In other embodiments, it is possible to use different tracking algorithms such as particle filtering, or Lucas-Kanade, as would be appreciated by a person of relevant skill in the art.

In an embodiment, the magnitude of velocity at which the extraction device moves towards the target specimen may be a pre-determined value. In a non-limiting example, the magnitude of this velocity is in the range of 0.1 centimeters per second to 2 centimeters per second. In an embodiment, the magnitude of velocity at which the extraction device attached to the robotic arm moves towards the target specimen may be varied according to the distance between the tip of the extraction device and the point on the target specimen closest to the extraction device. For example, an initial velocity of magnitude $v_1$ (e.g. 0.6 centimeters per second) may be used when the Euclidean distance between the tip of the extraction device and the point on the target specimen closest to the extraction device is larger than a distance threshold Δ, e.g. 1 cm, or during raversing the first half of the initial distance between the tip of the extraction device and the target specimen. The velocity may be subsequently decreased to $v_2$ (e.g. 0.3 centimeters per second), for example once it is determined that the Euclidean distance between the tip of the extraction device and the point on the target specimen closest to the extraction device is smaller than Δ, or during traversing the second half of the initial distance between the tip of the extraction device and the point on the target specimen closest to the extraction device. The gradual reduction in velocity magnitude may help the extraction process by reducing the possibility of further displacement of the target specimen as the extraction device gets closer to the target specimen. In an example, $v_2$ may be half of $v_1$. Other methods of varying the velocity of motion of the extraction device may also be used as recognized by a person of relevant skill in the art.

In an embodiment, the magnitude of velocity at which the extraction device attached to the robotic arm moves towards the target specimen is determined beforehand to minimize the displacement of specimens in the container as a result of the motion of the extraction device. The amount displacement of a specimen affected by the motion of the extraction device depends on the mass of the specimen. Consequently, specimens that have a higher mass experience smaller disposition.

In an embodiment, a priori information about the approximate mass of the specimens (or their order of magnitude), the particular type of extraction device, and the density of the liquid within the container are known. In this embodiment, the velocity of motion of a particular extraction device may be determined experimentally such that the dislocation of specimens is avoided or minimized.

In an embodiment, the magnitude of velocity at which the extraction device moves towards the target specimen is determined such that it avoids creating turbulence in the liquid within the container. For example, the magnitude of velocity may be determined such that the Reynold number is smaller than 1000. Reynold number is typically used to determine the state of a fluid (laminar or turbulent) and is calculated as below:

$$R_e = \rho v L / \mu$$

wherein $R_e$ is the Reynold number, $\rho$ is the density of the fluid (herein, the liquid within the container), L is a characteristic dimension (calculated based on the shape and size of the extraction device, and may be found in tabulated form for calculating Reynold number and drag coefficient for many geometrical shapes), and μ is the dynamic viscosity of the fluid (herein, the liquid within the container), as would be known and appreciated by a skilled artisan.

In an embodiment, the frame rate at which imaging units, e.g. imaging units 330 and 340 capture image frames (video frames) may be adjusted according to the magnitude of velocity of the extraction device. For example, if the velocity magnitude determined for the motion of the extraction device is reduced to half, the frame rate may be reduced to half as well.

In an embodiment, if a specimen extraction device does not find a target specimen after a predetermined amount of search time (e.g. 15 seconds), it is retreated from the container, allowing specimens to resettle stably in their positions. In an example, a pre-determined amount of settling time, such as one minute, may be used during which the specimen extraction device remains outside the container before re-entering. Subsequently, the process illustrated in FIG. 4 is resumed to recalculate the depth and position of the target specimen, and the extraction device is re-entered into the container to move to the new estimated location of the target specimen within the container.

In another embodiment, if a specimen extraction device does not find a target specimen after a predetermined amount of search time, the specimen extraction device remains in its place for a pre-determined amount of rest time, such as one minute, allowing the specimens to resettle in the container. Subsequently, recalculating the depth and position of the target specimen is performed, incorporating information of the location and shape of the extraction device, in order to exclude the extraction device from being identified as one or more specimens. The extraction device is subsequently moved to the new estimated location of the target specimen within the container.

Each of the processes and modules 310-340 and 370 in FIG. 3A may be implemented in hardware, software, firmware, or any combination thereof. Additionally, steps described in FIG. 4 and FIG. 8 may be implemented in hardware, software, firmware, or any combination thereof using images obtained from imaging devices as input. Furthermore, the operation of hardware elements, e.g. an extraction device that may be attached to a robotic arm, may be controlled by hardware, software, firmware, or any combination thereof.

Each of the processors and modules 310-340 and 370 in FIG. 3A, and steps described in FIG. 4 and FIG. 8 may be implemented on the same or different computing devices. Such computing devices can include, but are not limited to, a personal computer, a mobile device such as a mobile phone, workstation, embedded system, game console, television, set-top box, or any other computing device. Further, a computing device can include, but is not limited to, a device having a processor and memory, including a non-transitory memory, for executing and storing instructions. The memory may tangibly embody the data and program instructions. Software may include one or more applications and an operating system. Hardware can include, but is not limited to, a processor, a memory, and a graphical user interface display. The computing device may also have multiple processors and multiple shared or separate memory components. For example, the computing device may be a part of or the entirety of a clustered or distributed computing environment or server farm.

Identifiers, such as "(a)," "(b)," "(i)," "(ii)," etc., are sometimes used for different elements or steps. These identifiers are used for clarity and do not necessarily designate an order for the elements or steps.

The present invention has been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present invention should not be limited by any of the above-described exemplary embodiments, but should be defined only in accordance with the following claims and their equivalents.

What is claimed is:

1. A method for automatically extracting biological specimens from a container, comprising:
   obtaining one or more intrinsic and extrinsic properties of a first imaging system and a second imaging system,
   (ii) periodically imaging the container using the first imaging system and the second imaging system,
   (iii) simultaneously guiding an extraction device and tracking a target biological specimen from a plurality of biological specimens in the container using a plurality of images obtained from the first imaging system and the second imaging system, and
   (iv) extracting the target biological specimen from the container using the extraction device,
   wherein the container contains a transparent liquid,
   wherein the target biological specimen resides in the liquid in the container,
   wherein the extraction device is attached to a robotic arm,
   wherein the robotic arm is communicatively coupled to a processing unit,
   wherein the first and second imaging system are communicatively coupled to the processing unit, and
   wherein the first and second imaging systems are spatially separated, and
   wherein the first and second imaging systems image the container simultaneously and at a pre-determined frame rate, and
   wherein the target biological specimen is selected from the plurality of biological specimens by performing steps comprising:
   (a) performing image rectification on a first image obtained from the first imaging system and a second image obtained from the second imaging system using the intrinsic and extrinsic properties of the first and second imaging system obtained in (i), wherein the first and second image are obtained simultaneously,
   (b) obtaining a correspondence between a plurality of points in the first image and a plurality of points in the second image,
   (c) generating a disparity map based on the correspondence obtained in (b),
   (d) calculating a three-dimensional scene structure for a point in the plurality of points in the first image and a corresponding point in the plurality of points in the second image at least based on:
a priori information about the first and second imaging systems,
the intrinsic and extrinsic properties of the first imaging system and the second imaging system obtained in (i),
information on relative position and direction of the first imaging system and the second imaging system, and
the disparity map generated in (c),
(e) identifying and locating the plurality of specimens by combining the three-dimensional scene structure and edge detection,
(f) selecting the target biological specimen from the plurality of biological specimens based on the locating the plurality of biological specimens, and wherein the simultaneously guiding the extraction device and tracking the target biological specimen (iii) comprises:
simultaneously moving the extraction device attached to the robotic arm towards the target biological specimen, tracking a location of the target biological specimen, and tracking a location of a tip of the extraction device while the extraction device moves toward the target biological specimen,
wherein the tracking the location of the target biological specimen and the tracking the location of the tip of the extraction device are performed using consecutive images obtained from the first imaging system and consecutive images obtained from the second imaging system comprises:
tracking the location of the target biological specimen and the location of the extraction device in a horizontal plane based on consecutive images from the first imaging system, and
tracking the location of the target biological specimen and the location of the tip of the extraction device in a vertical direction by calculating a depth of the target biological specimen and a depth of the tip of the extraction device using consecutive images obtained from the first imaging system and consecutive images obtained from the second imaging system by repeatedly and upon receiving new images from the first imaging system and the second imaging system, performing steps comprising:
(A) performing image rectification on a first most recent image obtained from the first imaging system and a second most recent image obtained from the second imaging system, using the intrinsic and extrinsic properties of the first and second imaging system obtained in (i), wherein the first most recent image and the second most recent image are obtained simultaneously,
(B) obtaining the correspondence between a plurality of points in the first most recent image and a plurality of points in the second most recent image,
(C) generating a disparity map based on the correspondence between the first most recent image and the second most recent image obtained in (B),
(D) calculating a current three-dimensional scene structure for a point in the plurality of points in the first most recent image and a corresponding point in the plurality of points in the second most recent image based at least on:
a priori information about the first and second imaging systems,
the intrinsic and extrinsic properties of the first imaging system and the second imaging system obtained in (i),
the information on the relative position and direction of the first imaging system and the second imaging system, and
the disparity map generated in (C), and
(E) identifying the location of the target biological specimen and the tip of the extraction device in the vertical direction by combining the current three-dimensional scene structure and edge detection.

2. The method of claim 1, wherein the extraction device is moved at a pre-determined velocity magnitude.

3. The method of claim 1, wherein a density of each of the plurality of biological specimens within the container is smaller than a density of the liquid inside the container, and wherein the target biological specimen is selected to be a top-most biological specimen in the container.

4. The method of claim 1, wherein a density of each of the plurality of biological specimens within the container is greater than a density of the liquid inside the container.

5. The method of claim 4, wherein the target biological specimen is selected based on a solution to a traveling salesman problem, wherein the location of a point located on each of the plurality of biological specimens within the container represents a vertex to be visited in the traveling salesman problem.

6. The method of claim 5, wherein a horizontal cross-section of each of the plurality of biological specimens is approximated by a basic geometrical shape, and
wherein for each of the plurality of biological specimens, a location of the center of mass of the basic geometrical shape approximating the horizontal cross-section of the biological specimen is used to represent the vertex to be visited in the traveling salesman problem.

7. The method of claim 1, wherein in addition to identifying and locating the plurality of biological specimens, step (e) further comprises:
calculating and recording a number of the plurality of biological specimens, and a size of each of the plurality of biological specimens.

8. The method of claim 1, further comprising:
(v) moving the extraction device, by the robotic arm, toward a location where a cassette is located, wherein the cassette is labeled with at least one of patient information or biological specimen information,
(vi) placing the target biological specimen inside the cassette using the extraction device, and
(vii) returning to step (i), until no more biological specimen is left inside the container.

9. The method of claim 1, wherein the tracking the location of the target biological specimen and the tracking the location of the extraction device are performed using mean shift algorithm.

10. The method of claim 1, wherein the tracking the location of the target biological specimen and the tracking the location of the extraction device are performed using particle filtering.

11. The method of claim 1, wherein the tracking the location of the target biological specimen and the tracking the location of the extraction device are performed using Lucas-Kanade method.

12. The method of claim 1, wherein the generating disparity map in (c) further comprises:

generating an initial sparse feature correspondence map, and performing local plane sweeps on the initial sparse feature correspondence map.

13. The method of claim 12, wherein generating disparity map further comprises using multi-scale point correspondence along edges within the first image and the second image.

14. The method of claim 1, wherein step (e) further comprises:

pruning short edges and filling discontinuities along edges using anisotropic contour completion, and using prior knowledge about a general size of each of the plurality of biological specimens to merge or split detected surfaces.

15. The method of claim 8, wherein a biological specimen with a detected surface area smaller than a pre-determined surface area is excluded from the extracting.

16. The method of claim 8, further comprising:

in response to not finding the target biological specimen by the extraction device during a first pre-determined duration of time:

retracting the extraction device from the container, allowing a second pre-determined amount of time to pass so that biological specimens settle in the container, and repeating steps (i) to (iv).

17. The method of claim 8, further comprising:

in response to not finding target biological specimen by the extraction device during a first pre-determined duration of time:

fixing the extraction device in a current location of the extraction device in the container, allowing a second pre-determined amount of time to pass so that biological specimens settle in the container, and repeating steps (i) to (iv), wherein the extraction device is excluded from being determined as one of the plurality of biological specimens.

18. The method of claim 2, wherein moving the extraction device attached to the robotic arm at the pre-determined velocity magnitude towards the target biological specimen comprises:

moving the extraction device in a first pre-determined velocity magnitude for a first fraction of the distance between a tip of the extraction device and a point on the target biological specimen closest to the tip of the extraction device, and moving the extraction device in a second pre-determined velocity magnitude for a second fraction of the distance between the tip of the extraction device and the point on the target biological specimen closest to the tip of the extraction device, wherein the second velocity magnitude is smaller than the first velocity magnitude.

19. A non-transitory program storage device tangibly embodying a program of instructions executable by at least one machine to implement a method for automatically extracting biological specimens from a container, the method comprising:

(i) obtaining one or more intrinsic and extrinsic properties of a first imaging system and a second imaging system, (ii) periodically imaging the container using the first imaging system and the second imaging system, (iii) simultaneously guiding an extraction device and tracking a target biological specimen from a plurality of biological specimens in the container using a plurality of images obtained from the first imaging system and the second imaging system, and (iv) extracting the target biological specimen from the container using the extraction device, wherein the container contains a transparent liquid, wherein the target biological specimen resides in the liquid in the container, wherein the extraction device is attached to a robotic arm, wherein the robotic arm is communicatively coupled to a processing unit, wherein the first and second imaging systems are communicatively coupled to the processing unit, and wherein the first and second imaging systems are spatially separated, and wherein the first and second imaging systems image the container simultaneously and at a pre-determined frame rate, and wherein the target biological specimen is selected from the plurality of biological specimens by performing steps comprising:

(a) performing image rectification on a first image obtained from the first imaging system and a second image obtained from the second imaging system using the intrinsic and extrinsic properties of the first and second imaging system obtained in (i), wherein the first and second image are obtained simultaneously, (b) obtaining a correspondence between a plurality of points in the first image and a plurality of points in the second image, (c) generating a disparity map based on the correspondence obtained in (b), (d) calculating a three-dimensional scene structure for a point in the plurality of points in the first image and a corresponding point in the plurality of points in the second image at least based on:

a priori information about the first and second imaging systems, the intrinsic and extrinsic properties of the first imaging system and the second imaging system obtained in (i), information on relative position and direction of the first imaging system and the second imaging system, and the disparity map generated in (c), (e) identifying and locating the plurality of biological specimens by combining the three-dimensional scene structure and edge detection, (f) selecting the target biological specimen from the plurality of biological specimens based on the locating the plurality of biological specimens, and wherein the simultaneously guiding the extraction device and tracking the target biological specimen (iii) comprises:

simultaneously moving the extraction device attached to the robotic arm towards the target biological specimen, tracking a location of the target biological specimen, and tracking a location of a tip of the extraction device while the extraction device moves toward the target biological specimen, wherein the tracking the location of the target biological specimen and the tracking the location of the tip of the extraction device are performed using consecutive images obtained from the first imaging system and consecutive images obtained from the second imaging system comprises:

tracking the location of the target biological specimen and the location of the extraction device in a horizontal plane based on consecutive images from the first imaging system, and tracking the location of the target biological specimen and the location of the tip of the extraction device in a vertical direction by calculating a depth of the target biological specimen and a depth of the tip of the extraction device using consecutive images obtained from the first imaging system and consecutive images obtained from the second imaging system by repeatedly and upon receiving new images from the first imaging system and the second imaging system, performing steps comprising:

(A) performing image rectification on a first most recent image obtained from the first imaging system and a second most recent image obtained from the second imaging system, using the intrinsic and extrinsic properties of the first and second imaging system obtained in (i), wherein the first most recent image and the second most recent image are obtained simultaneously, (B) obtaining the correspondence between a plurality of points in the first most recent image and a plurality of points in the second most recent image, (C) generating a disparity map based on the correspondence between the first most recent image and the second most recent image obtained in (B), (D) calculating a current three-dimensional scene structure for a point in the plurality of points in the first most recent image and a corresponding point in the plurality of points in the second most recent image based at least on:
a priori information about the first and second imaging systems,
the intrinsic and extrinsic properties of the first imaging system and the second imaging system obtained in (i),
the information on the relative position and direction of the first imaging system and the second imaging system, and
the disparity map generated in (C), and (E) identifying the location of the target biological specimen and the tip of the extraction device in the vertical direction by combining the current three-dimensional scene structure and edge detection.

20. The non-transitory program storage device of claim 19, wherein:
the tracking the location of the target biological specimen is performed using one of mean shift method, particle filtering method, and Lucas-Kanade method,
wherein generating disparity map in (c) further comprises using an initial sparse feature correspondence map, and performing local plane sweeps on the on the initial sparse feature correspondence map, and
wherein the edge detection in (e) comprises pruning short edges, filling discontinuities along edges using anisotropic contour completion, and using prior knowledge about a general size of each of the plurality of biological specimens to merge or split detected surfaces.

* * * * *